(12) United States Patent
Hersh et al.

(10) Patent No.: US 7,226,421 B1
(45) Date of Patent: Jun. 5, 2007

(54) METHOD OF CONTROLLING BLOOD PRESSURE CUFF DEFLATION

(75) Inventors: Lawrence T. Hersh, Tampa, FL (US); Sai Kolluri, Tampa, FL (US); Bruce A. Friedman, Tampa, FL (US); Richard Medero, Tampa, FL (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/290,272

(22) Filed: Nov. 30, 2005

(51) Int. Cl.
    *A61B 5/00* (2006.01)
(52) U.S. Cl. .................. 600/494; 600/490; 600/496
(58) Field of Classification Search ............... None
    See application file for complete search history.

(56) References Cited

U.S. PATENT DOCUMENTS

| | | |
|---|---|---|
| 4,349,034 A | 9/1982 | Ramsey, III |
| 4,360,029 A | 11/1982 | Ramsey, III |
| 4,543,962 A | 10/1985 | Medero et al. |
| 4,796,184 A | 1/1989 | Bahr et al. |
| 4,889,133 A | 12/1989 | Nelson et al. |
| 4,949,710 A | 8/1990 | Dorsett et al. |
| 5,052,397 A * | 10/1991 | Ramsey et al. ............. 600/495 |
| 5,590,662 A | 1/1997 | Hersh et al. |
| 5,704,362 A | 1/1998 | Hersh et al. |
| 6,358,213 B1 | 3/2002 | Friedman et al. |
| 6,440,080 B1 | 8/2002 | Booth et al. |

OTHER PUBLICATIONS

"Blood Pressure Monitoring: Automated Oscillometric Devices", Maynard Ramsey III, Journal of Clinical Monitoring, 1991, 7(1), pp. 56-67.

* cited by examiner

*Primary Examiner*—Robert L. Nasser
(74) *Attorney, Agent, or Firm*—Andrus, Sceales, Starke & Sawall, LLP

(57) ABSTRACT

A method of operating a non-invasive blood pressure (NIBP) monitor that includes a blood pressure cuff and a pressure transducer. The method initially inflates the blood pressure cuff to a level above systolic pressure and begins to deflate the pressure cuff using a continuous or linear deflation technique. During the linear deflation of the pressure cuff, the oscillation pulses from the pressure transducer are obtained and compared to predicted pulse estimates. If the obtained oscillation pulses vary from the predicted pulse estimates, the linear deflation technique is interrupted and the pressure cuff is then deflated in a sequence of distinct pressure steps. During each pressure step, the oscillation pulses are obtained and the pressure cuff is not deflated to the next pressure step until the oscillation pulses correspond to each other.

14 Claims, 4 Drawing Sheets

METHOD OF CONTROLLING BLOOD PRESSURE CUFF DEFLATION

BACKGROUND OF THE INVENTION

The present invention generally relates to a method of controlling the operation of an automatic, non-invasive blood pressure (NIBP) monitor. More specifically, the present invention relates to a method of controlling the operation of a NIBP monitor to utilize both a linear deflation technique and step deflation technique to determine blood pressure.

Automated blood pressure monitors employ an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith and incorporated by reference, employs the oscillometric methodology.

In accordance with the Ramsey patents, an inflatable cuff is suitably located on the limb of a patient and is pumped up to a predetermined pressure above the systolic pressure. The cuff pressure is then reduced in predetermined decrements, and at each level, pressure fluctuations are monitored. The resultant arterial pulse signals typically consist of a DC voltage with a small superimposed variational component caused by arterial blood pressure pulsations (referred to herein as "oscillation complexes" or just simply "oscillations"). The oscillation amplitudes measured from the cuff can range from a fraction of a mmHg to as much as 8 mmHg.

After suitable filtering to reject the DC component and to provide amplification by a scale factor, peak oscillation amplitudes measured above a given base-line are stored. As the cuff pressure decrementing continues, the peak amplitudes will normally increase from a lower level to a relative maximum, and thereafter will decrease. These amplitudes form an oscillometric envelope for the patient. The lowest cuff pressure at which the oscillations have a maximum value has been found to be representative of the mean arterial pressure (MAP) of the patient. Systolic and diastolic pressures can be derived either as predetermined fractions of the oscillation size at MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator usually sets a time interval, typically from 1 to 90 minutes, at which blood pressure measurements are to be made. The noninvasive blood pressure (NIBP) monitor automatically starts a blood pressure determination at the end of the set time interval.

Generally, conventional NIBP monitors of the type described in the afore-mentioned patents use oscillation pulse amplitude matching at each pressure level as one of the ways to discriminate good oscillations from artifacts. In particular, pairs of oscillation pulses are compared at each pressure level to determine if they are similar in amplitude and similar in other attributes, such as shape, area under the oscillation curve, slope, and the like. If the oscillation pulses compare within predetermined limits, the average pulse amplitude and cuff pressure are stored and the pressure cuff is deflated to the next pressure level for another oscillation measurement. However, if the oscillation pulses do not compare favorably, the attributes of the earlier oscillation are typically ignored and the attributes of the latter oscillation are stored. The monitor does not deflate; instead, the monitor waits for another oscillation to compare with the one that was stored. This process continues until two successive oscillation pulses match or a time limit is exceeded.

Although the step deflation technique described above can eliminate or reduce the effect artifacts have in the blood pressure determination, the step deflation technique typically requires the detection of two oscillation pulses during each pressure step. Sometimes under artifact free circumstances an attempt can be made to obtain only one pulse at each step; however, there are still time inefficiencies even in this case. Even when the detected oscillation pulses are very clean and artifact free, the step deflation technique has an inherent delay in order to control the pressure level of each step. Therefore, the amount of time required to make a blood pressure determination will be extended by the time that the technique uses at each pressure step to control the pressure.

An alternate method of obtaining a blood pressure measurement is to operate the NIBP monitor using a continuous deflation from an initial inflation pressure to a final pressure. Typically, the recommended continuous deflation pattern is linear. During the linear deflation, the cuff pressure is decreased at a specific rate (mmHg/second) and the oscillation pulse amplitudes are measured for the cuff pressure as the pressure is continuously decreased. Since, in the case when the oscillometric signal is not corrupted by artifact, the NIBP system does not need to maintain pressure at a defined step to obtain high quality pulses, an NIBP system utilizing the linear deflation technique can often obtain a blood pressure measurement more quickly than a system utilizing the step deflation technique. However, note that other factors, like pulse pressure and heart rate, do influence the time it takes to complete a blood pressure determination for either the linear or step deflate patterns.

However, since the pressure of the blood pressure cuff is deflated continuously, if any one of the oscillation pulses is inaccurate due to an artifact introduced by the patient or some other external variable, the linear deflation technique does not include a mechanism to compare recorded oscillation pulse amplitudes, as is possible when utilizing the step deflation technique. Therefore, it can be understood that operating an NIBP monitor utilizing either a step deflation technique or a linear deflation technique has relative drawbacks in certain types of situations. Selectively operating an NIBP monitor utilizing both the step deflation technique and the linear deflation technique would be an improvement over the state of the art.

SUMMARY OF THE INVENTION

The following describes a method for measuring and displaying the blood pressure of a patient utilizing a non-invasive blood pressure (NIBP) monitor that includes an inflatable and deflatable blood pressure cuff and pressure transducer. The method obtains a series of oscillation pulses from the pressure transducer of the NIBP monitor, which are utilized to develop an oscillometric envelope and estimate the patient's blood pressure.

Initially, the blood pressure cuff of the NIBP monitor is inflated to an inflation pressure above the systolic pressure for the patient. Once the pressure cuff is inflated to the initial inflation pressure, the central processor of the NIBP monitor begins to deflate the pressure cuff utilizing a continuous deflation technique. As noted previously, one possible way to continuously deflate the cuff is to use a linear pattern. The linear deflate can be accomplished with and by controlling a proportional deflate valve. However, other continuous patterns could be used just as effectively. For example, rather than maintaining a linear pattern the deflate valve could simply be opened and air allowed to escape without further control.

As the pressure cuff is linearly deflated, the NIBP monitor obtains a series of oscillation pulses from the pressure transducer. Each of the oscillation pulses from the pressure transducer is compared to a predicted pulse estimate. The predicted pulse estimates can be calculated utilizing various estimation techniques, such as a simple prediction of the size of the next pulse to be observed based trends in previous pulses, a period measurement between the pulses based upon the period between previous pulses or a predicted estimate of the pulse size based upon the pulse size at the same cuff pressure from a previous blood pressure measurement cycle. Various methods and algorithms are contemplated for specifying a predicted pulse estimate that can be utilized by the central processor for comparison to a measured oscillation at some particular cuff pressure.

If the central processor determines that the obtained oscillation pulse varies from the predicted pulse estimate by more than a given tolerance or percentage, the central processor interrupts the linear deflation technique and holds the pressure cuff at the current cuff pressure.

While the pressure cuff is held at the current pressure, the central processor obtains additional oscillation pulses that are compared to the predicted pulse estimate and to each other. If the additional oscillation pulses do not closely correspond to each other and to the predicted pulse estimate, the central processor holds the cuff pressure constant until at least two oscillation pulses closely correspond to each other. Values for the accepted oscillation pulses are then stored and utilized when calculating a blood pressure estimate from an oscillometric envelope.

Once acceptable oscillation pulses have been found, the central processor deflates the pressure cuff in a series of distinct pressure steps or it reverts to the continuous deflation technique depending on the quality of match with the predicted pulse estimate. If the central processor determines that the step deflation technique shall be used, the central processor waits for closely corresponding oscillation pulses before transitioning to the next pressure level or reverting to the continuous deflation technique. Thus, the central processor transitions from the continuous deflation technique to a pressure step deflation technique when the obtained oscillation pulses do not correspond to predicted pulse estimates.

If the central processor determines that the obtained oscillation pulses during the step deflation technique closely correspond to the predicted pulse estimate, the central processor can again transition to the continuous deflation technique and again compare the obtained oscillation pulses to predicted pulse estimates.

In this manner, the NIBP monitor is operated using the linear deflation technique unless the linear deflation technique is obtaining oscillation pulses that do not correspond to predicted pulse estimates. Only when the obtained oscillation pulses do not closely correspond to the predicted pulse estimates will the NIBP monitor be operated utilizing a step deflation technique, which is more effective in reducing error due to artifacts encountered during the blood pressure determination.

BRIEF DESCRIPTION OF THE DRAWINGS

The drawings illustrate the best mode presently contemplated of carrying out the invention. In the drawings.

DETAILED DESCRIPTION OF THE PREFERRED EMBODIMENT

Figure 1:
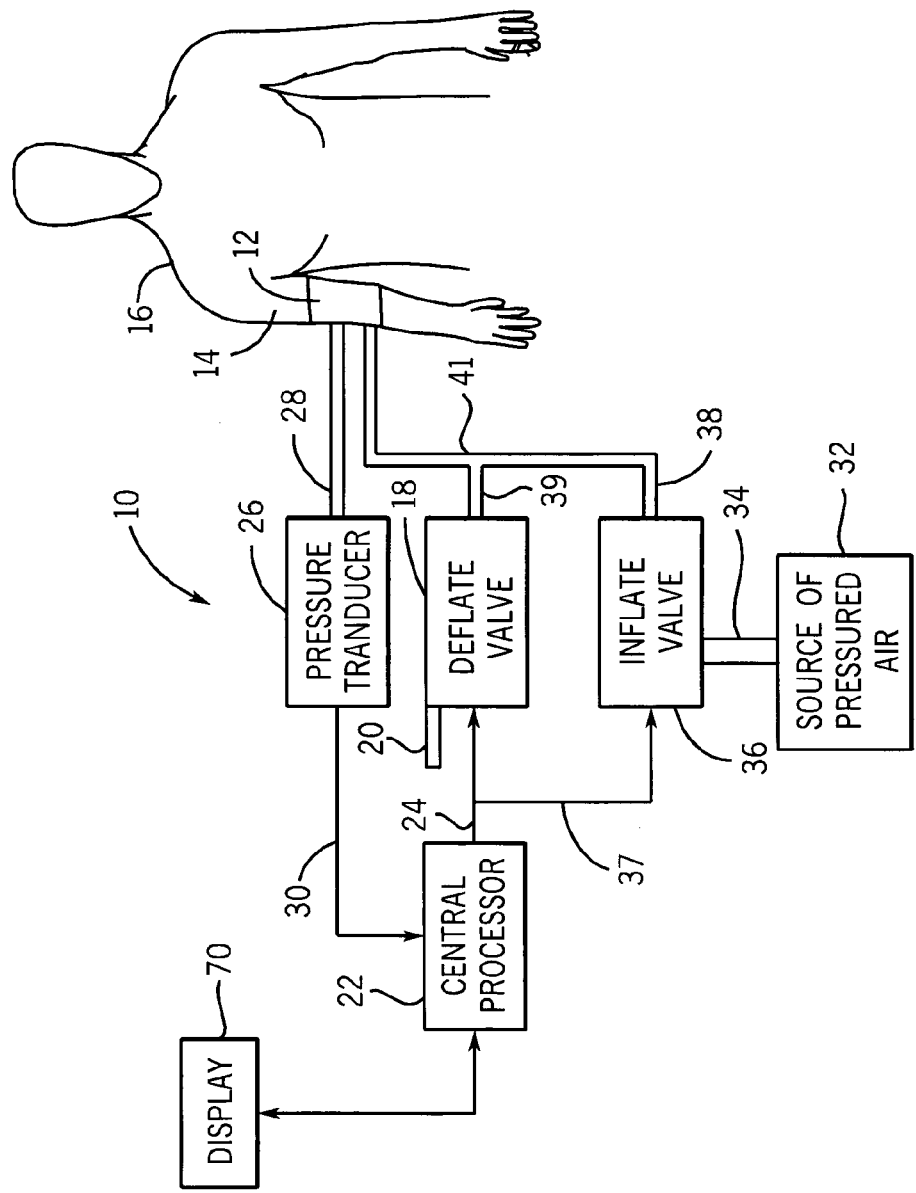
FIG. 1 is a high level diagram of a non-invasive blood pressure (NIBP) monitoring system.

FIG. 1 illustrates a simplified version of an oscillometric non-invasive blood pressure (NIBP) monitor 10 described in the aforementioned Ramsey patents. In FIG. 1, the arm 14 of a human patient 16 is shown wearing a conventional flexible inflatable and deflatable pressure cuff 12 for occluding the brachial artery when fully inflated. As the cuff 12 is deflated using deflate valve 18 having an exhaust 20, the arterial occlusion is gradually relieved. The deflation of cuff 12 via deflate valve 18 is controlled by central processor 22 via control line 24.

A pressure transducer 26 is coupled by a duct 28 to the pressure cuff 12 for sensing the pressure therein. In accordance with conventional oscillometric techniques, pressure oscillations in the artery are sensed by changes in the counter-pressure of the cuff 12, and these pressure oscillations are converted into an electrical signal by transducer 26 and coupled over path 30 to central processor 22 for processing. In addition, a source of pressurized air 32 is connected via a duct 34 through an inflate valve 36 and a duct 38 to the pressure cuff 12. The inflate valve 36 is electrically controlled through a connection 37 from the central processor 22. Also, the deflate valve 18 is connected by duct 39 via a branch connection 41 with the duct 38 leading to cuff 12.

During operation of the apparatus illustrated in FIG. 1, air under pressure at approximately 8–10 p.s.i. is typically available in the source of pressurized air 32. When it is desired to initiate a determination of blood pressure, the central processor 22 furnishes a signal over path 37 to open the inflate valve 36. The deflate valve 18 is closed. Air from the source 32 is communicated through inflate valve 36 and duct 38 to inflate the cuff 12 to a desired level, preferably above the estimated systolic pressure of the patient. Central processor 22 responds to a signal on path 30 from the pressure transducer 26, which is indicative of the instantaneous pressure in the cuff 12, to interrupt the inflation of the cuff 12 when the pressure in the cuff 12 reaches a predetermined initial inflation pressure that is above the estimated systolic pressure of the patient. Such interruption is accomplished by sending a signal over path 37 instructing inflate valve 36 to close. Once inflate valve 36 has been closed, the blood pressure measurement can be obtained by a deflation technique to be described below.

As is further described below, actual measurement of the blood pressure is accomplished by control from the central processor 22 using the deflate valve 18 and the pressure transducer 26. At the completion of each measurement cycle, the deflate valve 18 can be re-opened long enough to relax the cuff pressure via exhaust 20. Thereafter, the deflate valve 18 is closed for the start of a new measurement cycle.

Accordingly, when a blood pressure measurement is desired, the inflate valve 36 is opened while the cuff pressure is measured using the pressure transducer 26 until the cuff pressure reaches the desired level. The inflate valve 36 is then closed. Thereafter, the deflate valve 18 is controlled using signal 24 from central processor 22 and the blood pressure measurement taken.

Figure 2:
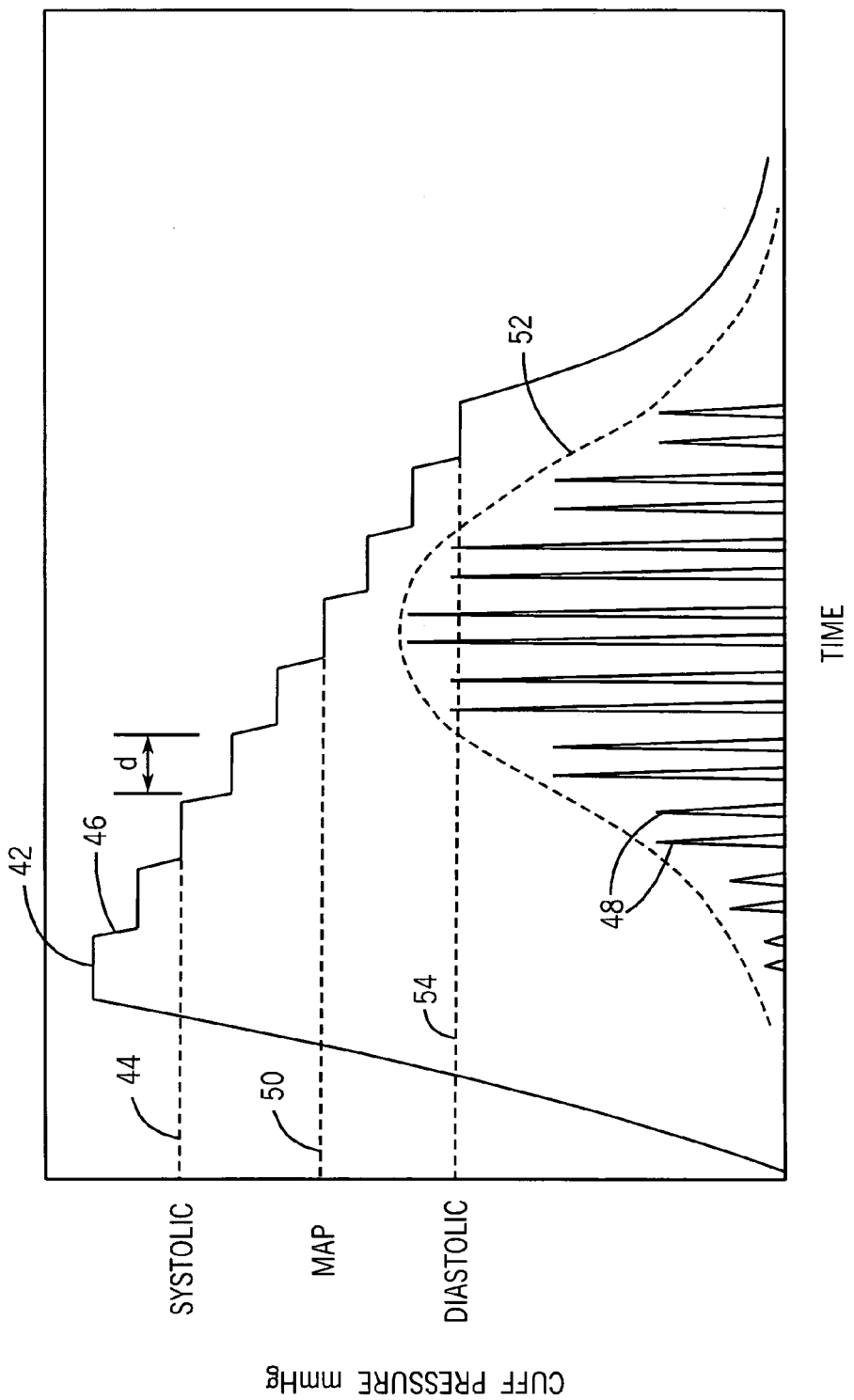
FIG. 2 illustrates oscillometric data including step deflate and oscillation pulse amplitudes derived using the NIBP monitoring system of FIG. 1.

FIG. 2 illustrates a pressure versus time graph illustrating a conventional cuff step deflation and measurement technique for a conventional NIBP monitor. As illustrated, the cuff is inflated to an initial inflation pressure 42 above the systolic pressure 44, and the cuff is then deflated to the next pressure level. A timeout duration, d, is provided at each step during which the signal processing circuitry searches for oscillation pulses 48 in accordance with the techniques described in the afore-mentioned commonly assigned patents or as described below. The cuff pressure is decremented before timeout duration, d, has elapsed if the detected oscillation pulses 48 closely correspond to each other, thereby indicating the lack of noise. This process of decrementing the pressure and searching for oscillation pulses is repeated until the oscillometric envelope 52 is sufficiently measured so that systolic, MAP 50, and diastolic may be calculated. The entire blood pressure determination process is then repeated at intervals set by the user, some other predetermined interval, or manually.

As shown in FIG. 2, the patient's arterial blood pressure forms an oscillometric envelope 52 comprised of a set of oscillation pulses 48 measured at each of the different cuff pressure steps. From the oscillometric envelope 52, systolic pressure 44, MAP 50 and diastolic blood pressure 54 are typically calculated. However, as noted in the afore-mentioned patents, it is desired that all artifact data be rejected from the measured data so that oscillometric envelope 52 contains only the desired data and no artifacts, thereby improving the accuracy of the blood pressure determinations.

Figure 3:
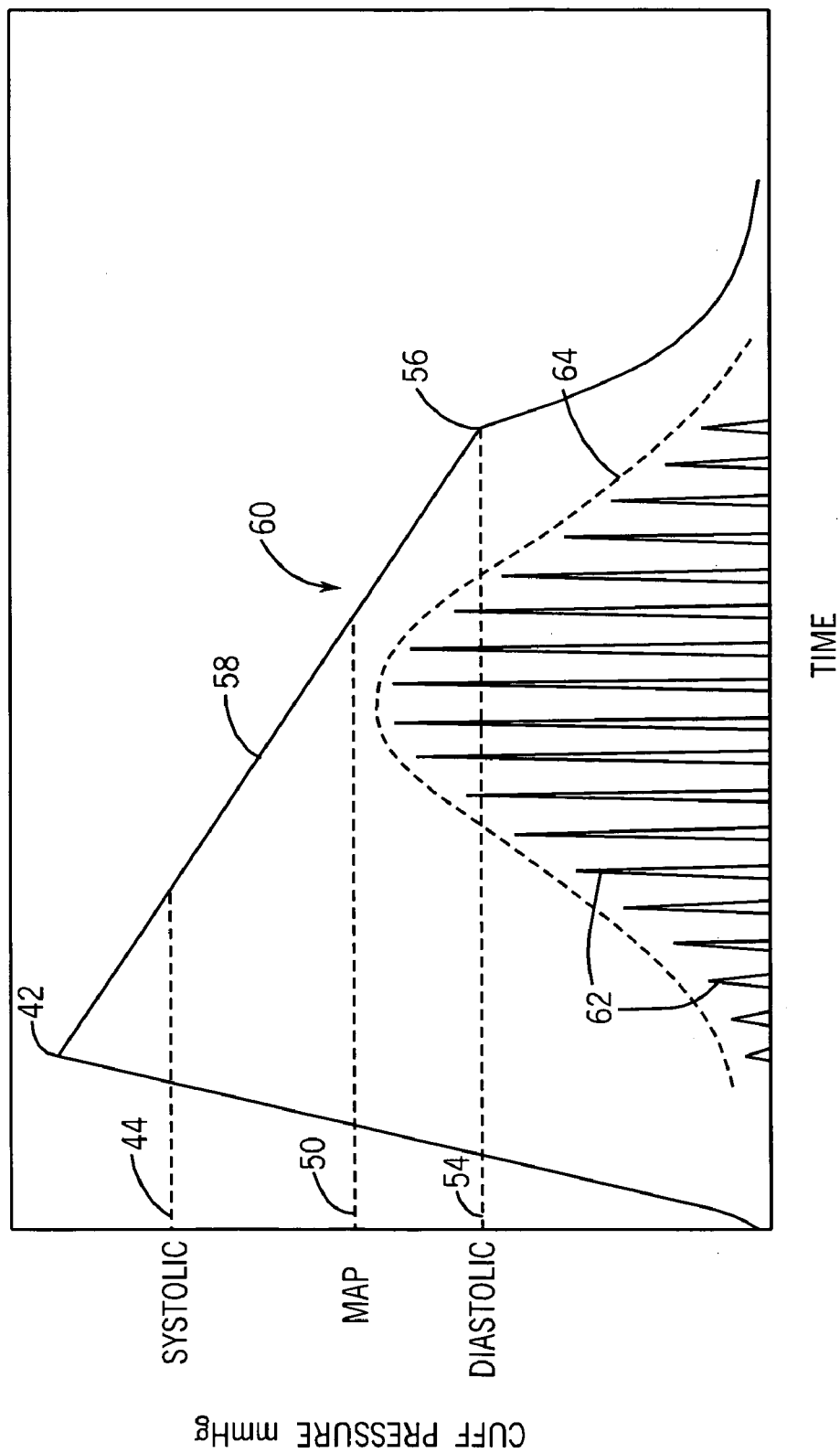
FIG. 3 illustrates oscillometric data including a linear deflate curve and oscillation pulse amplitudes derived using the NIBP monitoring system of FIG. 1.

FIG. 3 illustrates a pressure versus time graph illustrating the operation of a linear deflation and measurement technique for use with a conventional NIBP monitor. As illustrated, the pressure cuff is inflated to the initial inflation pressure 42 above the systolic pressure 44. Once the pressure cuff has reached the initial inflation pressure 42, the cuff pressure is then linearly decreased from initial inflation pressure 42 to a final pressure 56, as illustrated by the linear portion 58 of the pressure curve 60. As the cuff pressure decreases from the initial inflation pressure 42, the NIBP monitor detects and records each of the oscillation pulses 62 as well as the instantaneous pressure within the pressure cuff. The oscillation pulses 62 are recorded for the entire linear portion 58 of the pressure curve 60 from the initial inflation pressure to the final pressure 56.

As shown in FIG. 3, if the oscillation pulses are free of noise and artifacts, the oscillation pulses 62 form an oscillometric envelope 64 having a generally bell-shaped curve. From the oscillometric envelope 64, systolic pressure 44, MAP 50 and diastolic blood pressure 54 can be calculated. As described previously, the linear deflation technique shown in FIG. 3 allows the cuff pressure curve 60 to be decreased more rapidly from the initial inflation pressure 42 to the final pressure 56 as compared to the step deflection technique shown in FIG. 2. Thus, when little to no artifacts are present during the blood pressure measurement, it is often desirable to use the linear deflation technique shown in FIG. 3 with a more rapid deflation period to create the oscillometric envelope 64.

Although the linear deflation technique illustrated in FIG. 3 has proven to be a time effective technique to create the oscillometric envelope 64, the technique suffers when artifacts are introduced into the detection of the oscillation pulses, such as when the patient is being transported or during periods of a significant patient movement.

Figure 4:
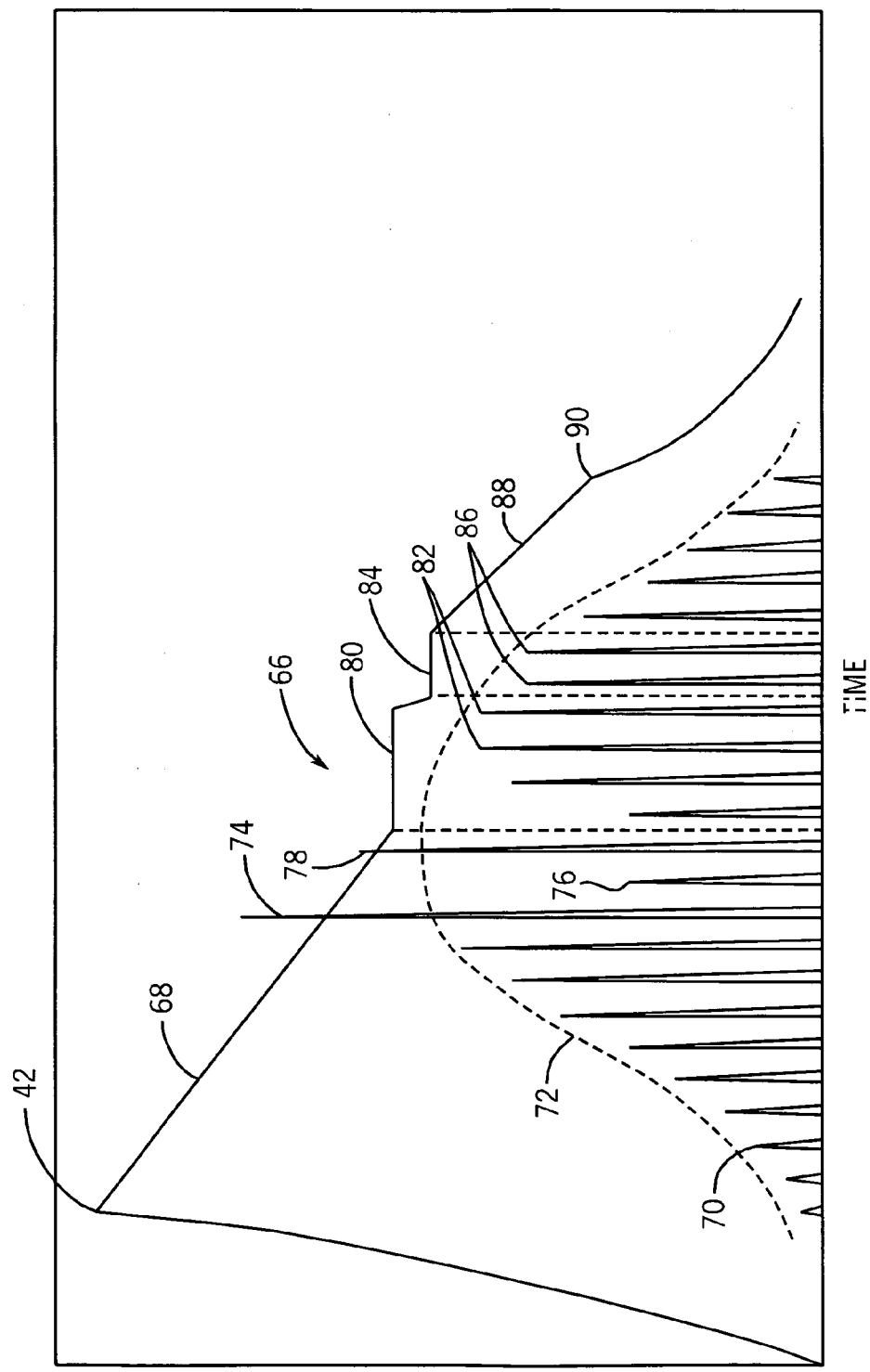
FIG. 4 illustrates oscillometric data obtained using both a linear deflation technique and a step deflation technique, including oscillation pulse amplitudes derived using the NIBP monitoring system of FIG. 1.

FIG. 4 illustrates a method of operating the NIBP monitor utilizing both the linear deflation technique as well as the step deflation technique to optimize the determination of a patient's blood pressure using an NIBP monitor. As shown in FIG. 4, the pressure cuff is initially inflated to a pressure 42 above systolic. Following the initial inflation, the pressure curve 66 for the cuff pressure is initially decreased using the linear deflation technique, as represented by the linear portion 68 of the cuff pressure curve 66. As the cuff pressure is decreased from the initial inflation pressure, the oscillation pulses 70 are recorded by the central processor. As the cuff pressure 66 continues to decrease along the linear portion 68, the central processor begins to construct the oscillometric envelope 72. In addition to beginning to develop the oscillometric envelope 72, the central processor evaluates each of the oscillation pulses 70 relative to predicted pulse estimates. The predicted pulse estimate can be determined using many different types of techniques, some of which will be described in detail below.

Referring back to FIG. 4, oscillation pulses 74, 76 and 78 clearly do not fall within a typical oscillometric envelope 72, primarily due to the presence of noise and artifacts. Once the central processor determines that the sensed pulses 74, 76 and 78 do not meet a predicted pulse profile, the central processor immediately interrupts the linear deflation of the pressure cuff. Upon interruption of this linear deflation, the central processor holds the cuff pressure constant and begins to control the NIBP monitor using the step deflation technique, as shown by the first pressure step 80. During the first pressure step 80, the central processor monitors the series of oscillation pulses until the oscillation pulses closely correspond to each other, as represented by the two pulses 82. As described previously, the central processor will not implement another step deflation until detecting at least two oscillation pulses that closely correspond. By operating the NIBP monitor using the step deflation technique, the central processor can discriminate good oscillation pulses from artifacts, unlike the operation utilizing the linear deflation technique.

In the embodiment of the invention illustrated in FIG. 4, the processor deflates the pressure cuff a second step 84 and again waits to detect multiple oscillation pulses that closely correspond to each other, as represented by oscillation pulses 86. Upon detection of the closely corresponding pulses 86, the central processor can either continue to deflate the pressure cuff using the step deflation technique or can again deflate the pressure cuff using the linear deflation technique, as represented by the second, linear portion 88 of the pressure curve 66. This decision could be made based on the nearness of agreement of the oscillation properties. If the comparison is within certain defined limits the deflate technique can be returned to a linear pattern. During the second, linear portion, the central processor again monitors the oscillation pulses and compares each of the obtained pulses to a predicted pulse estimate. If the detected pulses do not closely correspond to the pulse estimates, the central processor will again operate the NIBP monitor using the pressure step deflation technique. The central processor continues to deflate the pressure cuff to a final deflation pressure 90.

As can be understood in FIG. 4, the central processor of the NIBP monitoring system initially inflates the pressure cuff to an initial inflation pressure and monitors the oscillation pulses obtained during the linear deflation of the pressure within the cuff. During the linear deflation, the central processor monitors the detected oscillation pulses and compares the most recently detected pulse to a predicted pulse estimate for that cuff pressure. The creation of the predicted pulse estimates can be carried out using multiple different methods and techniques. Several techniques for generating the predicted pulse estimate will be set forth in detail below. However, it is should be understood that various other techniques of generating predicted pulse estimates can be utilized while operating within the scope of the present invention.

As discussed, once the detected pulse varies from the predicted pulse estimate by a certain value or percentage, the central processor switches the deflation of the pressure cuff from the linear deflation technique to the step deflation technique to more accurately make a blood pressure measurement in the presence of noise or artifacts. The method and technique of determining when the detected oscillometric pulses vary from a predicted pulse estimate is used to determine when the central processor switches from the linear deflation technique to the step deflation technique. Note that in general, there is no need to do a learning-step-deflate determination as the first determination, since techniques do exist for estimating the properties of the predicted pulses base solely on information obtained during the same determination. However, in some cases, particularly in high artifact circumstances, such a learning determination could easily be done.

In one embodiment of the invention, each oscillation pulse detected is used to predict the size of the next oscillation pulse to be observed. The predicted estimate for the size of the next pulse can be estimated based upon historic data from that particular patient or based upon general historical trends from other patients. The predicted size estimate for the next oscillation pulse is then compared to the actual, measured oscillation pulse received from the pressure transducer. If the actual, measured pulse size exceeds the estimated pulse size by more than a deviation percentage or value, the central processor will then switch from linear deflation to step deflation. In a preferred embodiment of the invention, the central processor will not switch from the linear deflation to the step deflation until at least two consecutive detected oscillation pulses deviate from the predicted estimates.

In another embodiment of the invention, the central processor estimates a predicted pulse period. The predicted pulse period is based upon the last two pulses actually detected by the central processor. Upon estimating the pulse period, the central processor will switch from linear deflation to step deflation when the actual pulse period deviates a predetermined amount or percentage from the predicted pulse period measurement. Once again, the central processor can trigger the transition from linear deflation to step deflation after either one variation from the predicted pulse period measurement or upon several consecutive deviations.

Another contemplated method of evaluating the detected oscillation pulses for determining whether to switch from linear deflation to step deflation involves generating a predicted estimate of the pulse size based upon the trend of the size of the last two pulses and a given tolerance. If the detected oscillation pulse exceeds the trend of the previous two pulses by more than a given tolerance, either above or below, the central processor will switch from linear deflation to step deflation. The tolerance value above and below the trend of the last two pulses will allow for both increasing and decreasing oscillation pulses within the general envelope shape.

Another embodiment of the method of determining whether to switch from linear deflation to step deflation involves utilizing historical data for the patient being monitored. Specifically, the oscillation pulse data obtained from the patient during the previous blood pressure determination can be utilized to create predicted estimates for the pulse sizes and other pulse properties during the current blood pressure measurement. If the current oscillation pulses do not correspond to the pulses during the last determination for the same cuff pressure within a given tolerance, the central processor can switch operation from linear deflation to step deflation. This type of technique is particularly desirable where the cycle time between blood pressure determinations is relatively small, thus eliminating large changes in the patient's blood pressure between measurements.

Another embodiment includes predicting the shape of the next oscillation pulse based upon the shape of the previous pulses detected. The system utilizes historical data from other patients to create a predicted pulse shape for the patient being monitored. If the detected oscillation pulses do not closely correspond to the predicted pulse shape, the central processor can switch from linear deflation to step deflation. Pulse shapes can be compared using correlation techniques are described in U.S. Pat. No. 5,590,662 by Hersh and Booth, the disclosure of which is incorporated herein by reference.

As can be understood by the previous description, the central processor of the NIBP monitoring system initially operates the NIBP system using a linear deflation technique. If, during the linear deflation of the blood pressure cuff, oscillation pulses are not within some small neighborhood of the predicted pulse estimates, the central processor will begin to operate the NIBP monitor using a step deflation technique. During the combined deflation utilizing both the linear deflation technique and the pressure step deflation technique, the central processor will store the oscillation pulses and cuff pressures to create an oscillometric envelope. However, during the combination of the linear deflation and step deflation, various artifacts may be recorded as part of the oscillation pulses. Thus, once the combined data from the linear deflation technique and the step deflation technique are stored within the central processor, the central processor can utilize curve fitting to generate a blood pressure for the patient. Curve fitting techniques are shown and described in U.S. Pat. No. 5,704,362, the disclosure of which is incorporated herein by reference.

Various alternatives and embodiments are contemplated as being within the scope of the following claims particularly pointing out and distinctly claiming the subject matter regarded as the invention.

What is claimed is:

1. A method of operating a non-invasive blood pressure (NIBP) monitor having an inflatable and deflatable pressure cuff positioned on a patient and using a pressure transducer, with the method comprising the steps of:

inflating the pressure cuff to an initial inflation pressure;

continuously deflating the pressure cuff from the initial inflation pressure;

obtaining a series of oscillation pulses from the pressure transducer as the pressure cuff is deflated from the initial inflation pressure;

comparing the obtained oscillation pulses to predicted pulse estimates;

interrupting the continuous deflation of the pressure cuff when the obtained oscillation pulses vary from the predicted pulse estimates;

deflating the pressure cuff in a sequence of distinct pressure steps after interruption of the continuous deflation;

obtaining oscillation pulses from the pressure transducer during each pressure step; and calculating the patient's blood pressure based on the plurality of obtained oscillation pulses.

2. The method of claim 1 wherein the step of comparing the obtained oscillation pulses to the predicted pulse estimates includes predicting the size of each oscillation pulse to be obtained based upon the prior obtained pulses and a predefined tolerance, wherein the continuous deflation is interrupted if the oscillation pulse is outside the tolerance around the predicted pulse estimate.

3. The method of claim 1 wherein the step of comparing the obtained oscillation pulses to the predicted pulse estimates includes comparing the obtained oscillation pulse to the oscillation pulse measured at the same cuff pressure during a previous blood pressure measurement cycle.

4. The method of claim 1 wherein at least two oscillation pulses are obtained during a pressure step, wherein the pressure cuff is deflated to the next pressure step only if the oscillation pulses obtained during that pressure step closely correspond to each other in magnitude or other pulse property.

5. The method of claim 4 further comprising the step of continuing to deflate the cuff using continuous deflation after the obtained oscillation pulses during a pressure step closely correspond to each other in magnitude or other pulse property.

6. The method of claim 1 wherein the patient's blood pressure is calculated using the oscillation pulses obtained during both continuous deflation and during the sequence of pressure steps.

7. The method of claim 1 further comprising the step of deflating the pressure cuff to a final pressure in the sequence of pressure steps following interruption of the continuous deflation.

8. A method of operating a non-invasive blood pressure (NIBP) monitor having an inflatable and deflatable pressure cuff positioned on the patient and a pressure transducer operable to detect oscillometric pulses, the method comprising the steps of:

deflating the pressure cuff from an initial inflation pressure to a final pressure using a continuous deflation technique;

obtaining oscillation pulses from the pressure transducer during the continuous deflation of the pressure cuff from the initial inflation pressure;

comparing the obtained oscillation pulses to predicted pulse estimates; and terminating the continuous deflation of the pressure cuff and deflating the pressure cuff in a series of pressure steps when the obtained oscillation pulses vary from the predicted pulse estimates.

9. The method of claim 8 further comprising the step of:

obtaining at least two oscillation pulses during each pressure step;

comparing the oscillation pulses obtained during a pressure step; and deflating the pressure cuff using the continuous deflation technique when the two oscillation pulses during that pressure step closely correspond to each other in amplitude or some other property.

10. The method of claim 8 wherein the step of comparing the obtained oscillation pulses to the predicted pulse estimates includes predicting the size of each oscillation pulse to be obtained based upon the prior obtained pulses and a predefined tolerance, wherein the continuous deflation is interrupted if the oscillation pulse size differs from the predicted pulse estimate.

11. The method of claim 8 wherein the step of comparing the obtained oscillation pulses to the predicted pulse estimates includes correlating the cuff pressure signal with a predetermined template representing attributes of a known blood pressure cuff oscillation.

12. The method of claim 8 wherein the step of comparing the obtained oscillation pulses to the predicted pulse estimates includes comparing the obtained oscillation pulse to the oscillation pulse measured at the same cuff pressure during a previous blood pressure measurement cycle.

13. The method of claim 8 wherein at least two oscillation pulses are obtained during a pressure step, wherein the pressure cuff is deflated to the next pressure step only if the oscillation pulses obtained during the pressure step correspond to each other with a specified tolerance.

14. The method of claim 13 further comprising the step of continuing to deflate the cuff using continuous deflation after the obtained oscillation pulses during a pressure step correspond to each other within a tighter specified tolerance.

* * * * *